United States Patent [19]
Cooper

[11] Patent Number: 4,883,494
[45] Date of Patent: Nov. 28, 1989

[54] SHIFT DEVICE FOR A PROSTHETIC LIMB

[75] Inventor: John E. Cooper, Leatherhead, United Kingdom

[73] Assignee: J. E. Hanger & Company Limited, London, England

[21] Appl. No.: 122,742

[22] Filed: Nov. 19, 1987

[30] Foreign Application Priority Data

Nov. 21, 1986 [GB] United Kingdom ............... 8627952

[51] Int. Cl.$^4$ ............................................. A61F 1/02
[52] U.S. Cl. .................................................. 603/39
[58] Field of Search ............................ 623/38, 39, 48

[56] References Cited

U.S. PATENT DOCUMENTS

| | | | |
|---|---|---|---|
| 3,273,168 | 9/1966 | Gardner et al. | 623/38 |
| 3,351,955 | 11/1967 | Middleton | 623/39 |
| 3,414,908 | 12/1968 | Waggot et al. | 623/38 |
| 3,422,462 | 1/1969 | Finnieston | 623/38 |
| 3,538,516 | 11/1970 | Bailey et al. | 623/48 |
| 3,671,978 | 6/1972 | May | 623/38 |
| 4,216,550 | 8/1980 | Thompson | 623/38 |
| 4,536,898 | 8/1985 | Palfray | 623/38 |

FOREIGN PATENT DOCUMENTS

| | | | |
|---|---|---|---|
| 2162069A | 10/1970 | United Kingdom | 623/39 |
| 1208421 | 1/1986 | United Kingdom | 623/39 |

Primary Examiner—Richard J. Apley
Assistant Examiner—David J. Isabella
Attorney, Agent, or Firm—Shoemaker and Mattare

[57] ABSTRACT

A shift device for a prosthetic limb comprises: first and second plates having adjoining flat faces in sliding contact. Spaced parallel ribs on an outer face of each plate define a slideway. Guides in the slideways of the first and second plates enable the plates to move generally at right angles to one another. The guides include first and second guide bars slideably received in the respective slideways. One or more longitudinal slots in each slideway permit limited relative translational movement of the plates. Clamping screws pass through each slot of each of the first and second plates into the guide bar in the slideway of the other plate. The clamping screws are releasable to allow relative movement of the plates and on re-tightening immobilize the plates.

14 Claims, 3 Drawing Sheets

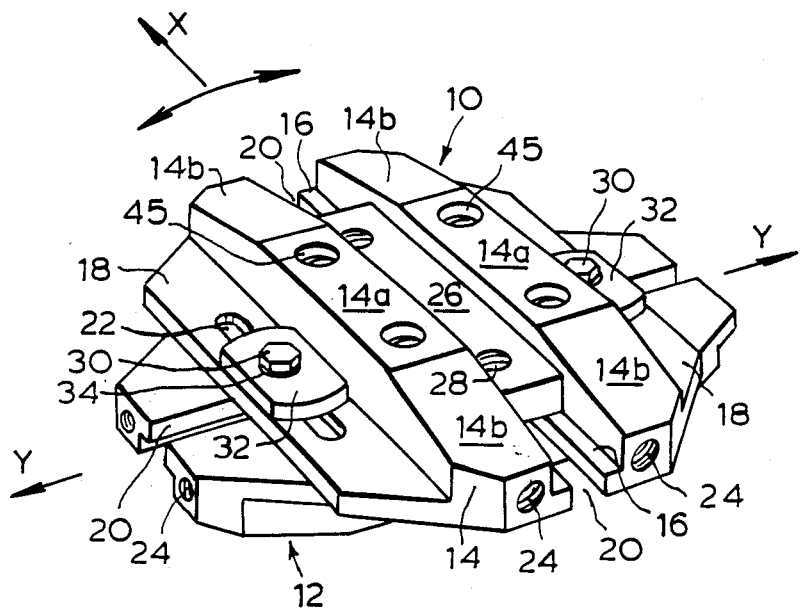
FIG. 2.
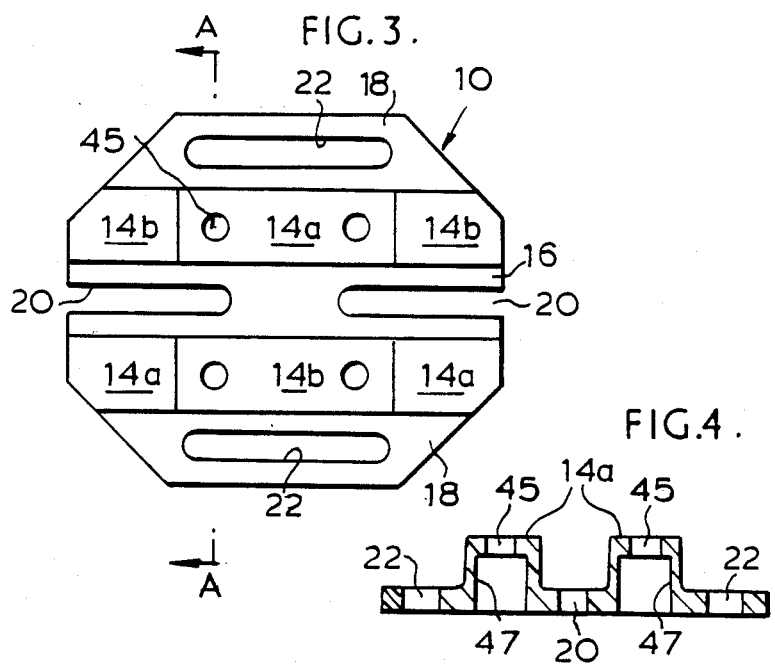
FIG. 3.
FIG. 4.

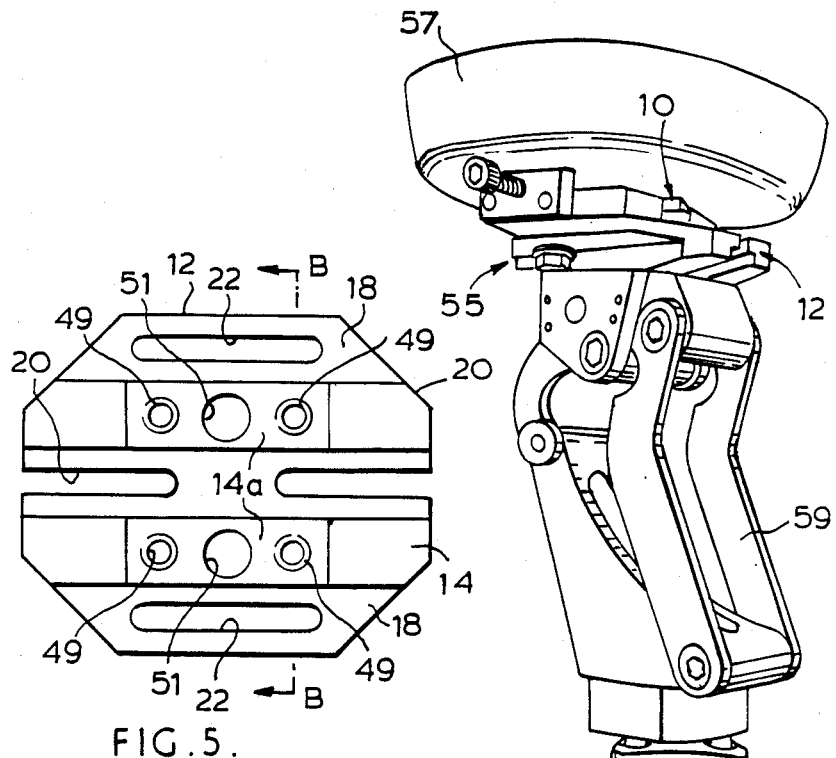
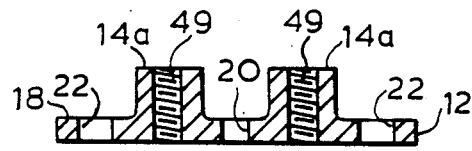
FIG.5.
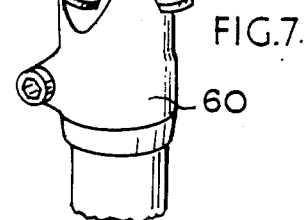
FIG.6.
FIG.7.
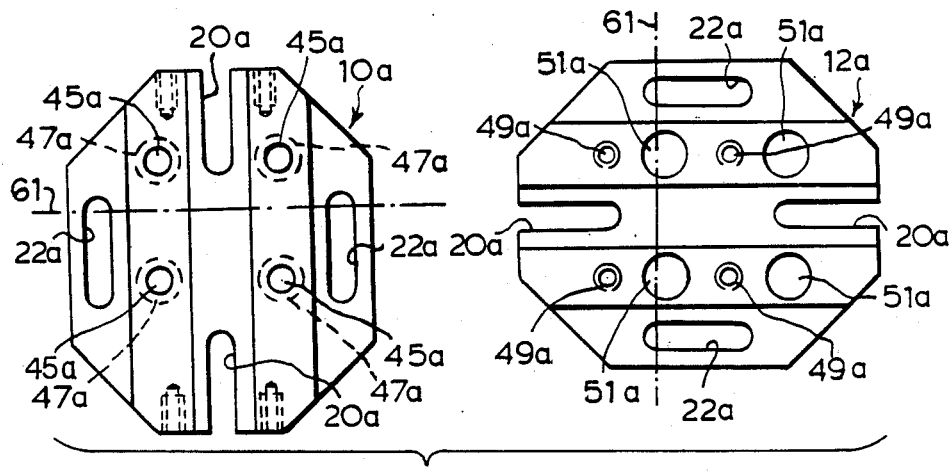
FIG. 8

SHIFT DEVICE FOR A PROSTHETIC LIMB

FIELD OF THE INVENTION

This invention relates to a shift device for a prosthetic limb, which is particularly though not exclusively intended for use as part of a prosthetic leg. Such a device produces a shift of its movable components in one plane without movement of the components in a direction orthogonal to that plane.

BACKGROUND OF THE INVENTION

A shift device that works by a combination of rotational and translational movements is described in Patent Specification No. GB-A-2162069 (Vessa). A shift device that works by a multiplicity of ribbed plates defining an orthogonal pair of linear bearings is described in Patent Specification No. GB-A-1028421 (Rubery Owen).

SUMMARY OF THE INVENTION

This invention provides a shift device whose principal components are a pair of plates each of the same fundamental form as the other and that can be released for relative movement and refixed simply by undoing and re-tightening clamping screws.

Accordingly the invention provides a shift device for a prosthetic limb comprising:

first and second plates having adjoining flat faces in sliding contact;

an elongated slideway extending across an ouyter face of each plate to end at edges of the plate;

means guiding the slideways of the first and second plates for movement generally at right angles to one another; said guiding means including first and second guide bars slideably received in each slideway;

means in each slideway defining at least one longitudinal slot whose length permits limited relative translational movement of the plates; and clamping screw located freely in each slot of each of the first and second plates and engaging the guide bar in the slideway of the other plate, said clamping screw being releasable to allow relative movement of the plates and on re-tightening immobilising the plates. The above device has the further advantage of occupying only a short distance along the limb.

DESCRIPTION OF PREFERRED FEATURES

Advantageously there are two open slots in each slideway extending from its ends partway therealong and each guide bar receives a pair of clamping screws located freely in the slots. Each plate may be flanged to either side of the slideway with elongated closed slots formed therein through which the clamping screws are freely located and Advantageously, the elongated closed slots are wider than the screws to permit limited relative rotational movement of the plates.

Each plate may be formed with attachment means, e.g., holes, by means of which adjacent limb parts can be attached thereto. A compact device may be made if each plate is formed with one hole, or a plurality, e.g., four plain side holes disposed in a pattern, e.g., a square that is offset relative to a pattern line of symmetry. of slots in the plate so that the plates are movable between one extremity of their relative travel when the fixing holes are aligned and other positions within the range of relative travel where the fixing holes are offset. The or each hole in the first plate may be plain-sided and have larger diameter counterbores on the face of the plate adjoining the other plate for receiving a head of a screw, the second plate having at least one plain sided holes having a diameter equal to the counterbore diameter and movable into register with the or each counterbore to permit insertion of a screw and allowing access for a tool such as a key or screwdriver to turn the or each screw located in the or each hole in said one plate.

For fine adjustment of the relative translational position of the first and second plates the shift device may be used in association with at least one jacking means attached to one of the plates at an end of a slideway and including a jacking screw registering with the guide bar therein for effecting controlled translational movement of the other plate. The jacking means are normally used in pairs attached to opposed ends of the slideway and may be removed when the prosthetist is satisfied with the alignment of the limb.

The invention also provides a prosthetic limb in which a shift device as aforesaid is fitted between a knee joint and upper parts of the leg such as a stump socket. An alignment device may then be attached between the knee joint and lower parts of the leg, said alignment device permitting adjustment of the angle between the knee and lower parts of the leg in an anterior-posterior and in a medial-lateral plane.

BRIEF DESCRIPTION OF THE DRAWINGS

Various embodiment of the invention will now be described, by way of example only, with reference to the accompanying drawings, in which:

FIGS. 1 and 2 are perspective views of a shift device according to the invention, shown exploded and assembled, respectively;

FIG. 3 is a plan of a clearance plate forming part of the shift device of FIGS. 1 and 2;

FIG. 4 is a transverse section of a first form of the plate on the line A-A of FIG. 3;

FIG. 5 is a plan of a tapped plate forming part of the shift device of FIGS. 1 and 2;

FIG. 6 is a transverse section of the plate on the line B—B of FIG. 5;

FIG. 7 is a side view of the knee region of a leg prosthesis showing a socket cup, shift device, prosthetic knee and alignment device; and FIG. 8 is a view of a pair of plates of a second form.

DETAILED DESCRIPTION OF PREFERRED EMBODIMENT

Figure 1:
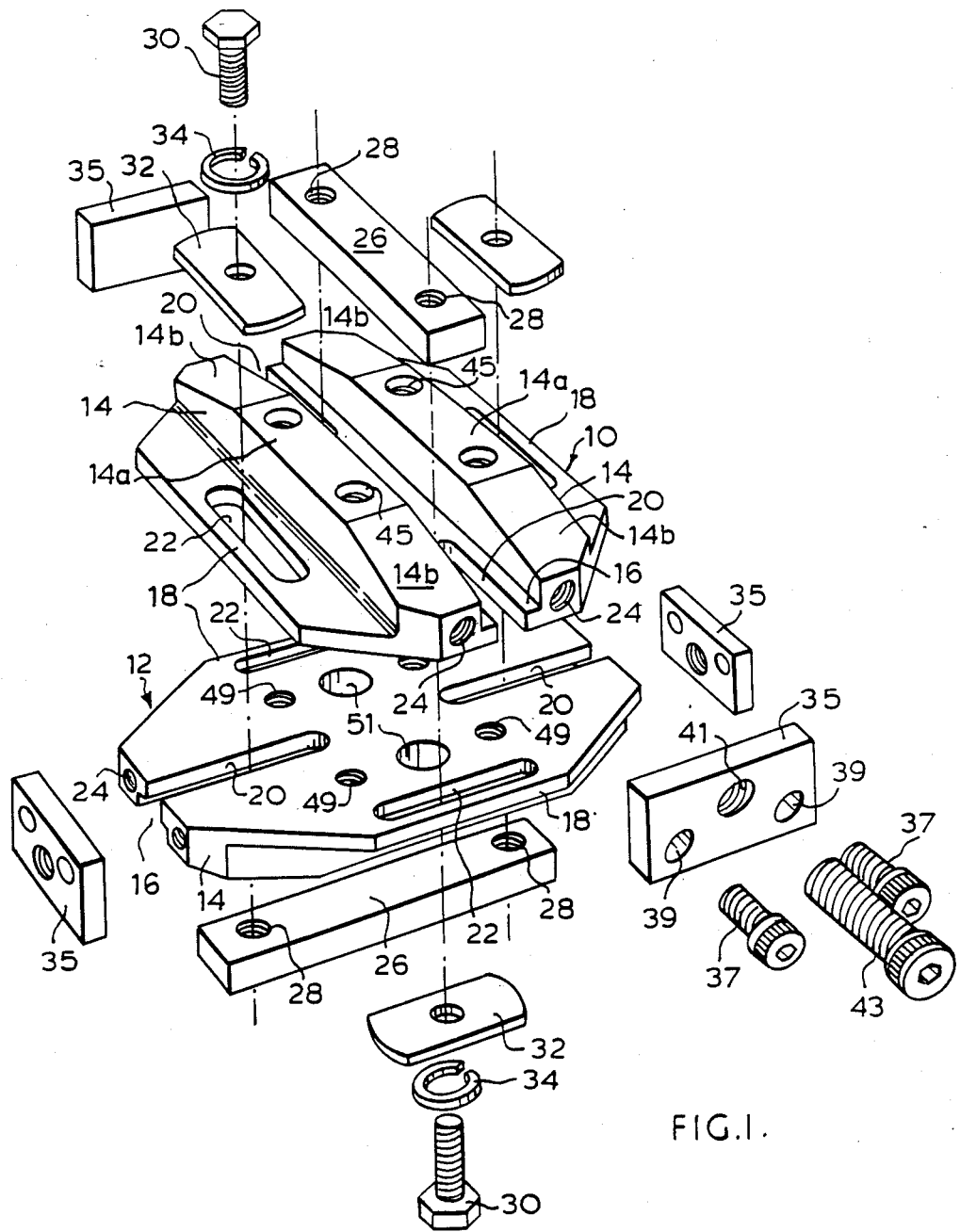

In the drawings, a shift device for a prosthetic limb comprises first and second plates 10, 12 each generally octagonal in plan and having adjoining planar faces in sliding contact with one another. Each plate 10, 12 has on its visible face a central elongated slideway 16 extending across each plate to end at the edges of the plate, each slideway 16 being defined between a pair of spaced parallel ribs 14 that extend across the plate. Each rib 14 has a flat central region 14a and tapered end regions 14b. Beyond the ribs 14 the plates 10, 12 are formed with side flanges 18.

Open slots 20 extend from the ends of the slideway 16 at the edge of the plates partway towards its middle and are directed along the centre line of the slideway. The flanges 18 are formed with elongated, closely oval slots 22 midway therealong and directed parallel to the ribs 14. End bores 24 are formed in the ribs 14.

In the assembled device the plates 10, 12 are superposed with their slideways 16 directed generally at right angles to one another and with the slots 16 of one plate in register with the slots 22 of the other plate. A guide bar 26 with threaded holes 28 adjacent its ends has a sliding fit in each slideway 16. Clamping screws 30 fit from the visible face of one plate 10, 12 through slots 22 of that plate and through slots 20 of the other plate 12, 10 into the guide bar 26 of the other plate 12, 10 where they are inserted into the holes 28. A thrust plate 32 and spring washer 34 fit on the stem of each screw 30. Each plate is capable of a limited translational movement relative to the other in an X or Y direction on release of the screws 30 which slide along the slots 20, 22, the plates 10, 12 being movable in either direction at 90° independently of each other. They can also rotate, preferably by about ±10° with respect to each other because the slots 22 are made wider than the stems of the screws 30. Retightening the screws urges the plates 10, 12 together so that the friction of their abutting surfaces prevents further movement. It will be noted that the plates 10, 12 are identical except for the mounting hole details described below and all the slots 20, 22 and slideway 16 are straight and parallel.

During setting up of the limb it is desirable to provide a fine adjustment for use by the prosthetist. For this purpose a jack plate 35 is attached to either end of a plate 10 or 12 by insertion of bolts 37 through plain-sided holes 39 into the bores 24. A further, threaded hole 41 in the plate 35 is aligned with the slideway 16 so that a jacking screw 43 may be brought into contact with an end of the guide bar 26 and thereafter tightened to displace the guide bar 26 as required. Although a single jacking assembly is sufficient to displace one guide bar 26 in one direction at a time, they are conveniently used in pairs with one jacking screw 43 being rotatably moved and thereby loosened while the other is also rotatably moved and thereby tightened. Furthermore, a pair of jacking devices fitted to adjacent ends of the plates 10, 12 preserves a predetermined X and Y dimension if the shift device is subsequently freed or disassembled, although rotational position is not preserved.

The structure of the first plate 10 is further shown in FIGS. 3 and 4. Each region 14a of the means 14 is formed with a pair of clearance holes 45 from its visible face to accept threaded shanks of clamping screws whose heads are inserted from the blind face into relatively large diameter counterbores 47. FIGS. 5 and 6 show the structure of the second plate 12 which is formed in its regions 14a with two pairs of threaded bores 49. Midway between the holes 49 of each pair a plain-sided-hole 51 is formed in the region 14a, the diameter of the hole 51 (FIG. 5) being equal to that of the counterbore 47. In the assembled shift device the plates 10, 12 can be slid so that the holes 51 register with each pair of counterbores 47 in turn, permitting a screw to be inserted via a hole 51 into the counterbore 47 and clearance hole 45. There is then access for a tool such a a screwdriver or key through the hole 51 to the head of the screw which may be engaged in and tightened into a threaded bore of an adjacent limb component. This arrangement permits the shift device to be fitted to a component such as a knee prosthesis where restricted tool access does not permit screws to be iserted through the component into threaded bores like the bores 49 of plate 12.

As shown in FIG. 7, the shift device of the invention generally indicated by the reference numeral 55 may advantageously be used between a socket attachment cup 57 and the top member of a prosthetic knee 59 to permit the axis of the socket to be shifted in an anterior/posterior plane and/or in a medial lateral plane and/or to be rotated relative to the knee. Such a knee may be a uniaxial knee as described in assignee's co-pending U.S. patent applications Ser. No. 038,612, now abandoned, and refiled as continuation-in-part application Ser. Nos. 236,733, and 917,976, now U.S. Pat. No. 4,756,713 or it may be a 4-bar knee as also described in Ser. No. 038,612. It has the advantage of occupying a short axial length along the leg which means that it can be used for many patients of differing stump length without undue displacement of the prosthetic knee centre from its height in the natural leg. The underside of the knee unit may be provided with an alignment device 60, conveniently a ball and socket device as described in assignee's co-pending U.S. Patent Application Ser. No. 933,176 now U.S. Pat. No. 4,728,336, the female part of the device being attached to the knee and the male part of the device having a socket that fits onto a shin tube. The shift device may also be used between a socket and a shin part of an artificial leg for a below-knee amputee.

It will be appreciated that modifications may be made to the embodiment described above without departing from the invention, the scope of which is defined in the appended claims. For example, a second form of the shift device is shown in FIG. 8. It may be noted in FIG. 3 that the pattern of clearance holes 45 and counterbores 47 defining an attachment position for upper or lower limb components is positioned at the centre of plate 10, 12 and is symmetrically located with reference to the slots 20, 22. The position where the holes 45 of one plate are disposed coaxially with the holes of the other plate is seen in FIG. 2 and it may be seen that displacement of plate 10 or 12 in either direction from that position is catered for. It has been found that the provision of such bidirectional adjustment is unnecessary and that a more compact form of the plates 10a, 12a (FIG. 8) may be made in which the slots 20a, 22a are half the length shown in FIGS. 3 and 5 and the imaginary line of symmetry 61 joining mid points of two opposite sides of the square pattern of fixing holes 45a, 49a is offset relative to the central line of symmetry drawn across elongated oval slots 22a. With this arrangement, displacing the plates 10a, 12a so that the clamping screws 30 (FIG. 1) from one end of the elongated oval slots 22 to another moves the counterbore 47a of plate 10a and bore 49a of plate 12a from an aligned condition to a displaced position. For a maximum displacement in X and Y directions of x and y, the plates establish a displacement vector between (O, O) and (x, y). Displacement vectors in the other three quadrants (x,−y); (−x, y); and (−x−y) can be obtained by removing the alignment device from the upper and lower limb components and re-fastening it in a new one of the four possible positions defined by fixing holes or bores 47a, 49a.

I claim:
1. A shift device for a prosthetic limb, comprising:
first and second plates having adjoining flat faces in sliding contact;
an elongated slideway extending across an outer face of each plate and ending at respective edges of the plate;

guiding means for guiding the slideways of the first and second plates for movement generally at right angles to one another, said guiding means including first and second bars slideably received in a respective slideway;

means in each slideway defining at least one longitudinal slot whose length permits limited relative translational movement of the plates; and a clamping screw located freely in each slot of each of the first and second plates and engaging the guide bar in the slideway of the other plate, said clamping screw being releasable to allow relative movement of the plates and on re-tightening immobilising the plates.

2. A device according to claim 1, wherein:
there are two slots in each slideway extending from its ends partway therealong, and each guide bar receives a pair of clamping screws located freely in the slots.

3. A device according to claim 2, wherein:
each plate is flanged to either side of the slideway, and each flange has an elongated closed slot through which the clamping screws pass.

4. A device according to claim 3, wherein:
the elongated closed slots are wider than each screw to permit limited relative rotational movement of the plates.

5. A device according to any preceding claim, wherein:
each plate has attachment means by which adjacent limb parts can be attached thereto.

6. A device according to claim 1, further comprising:
at least one jacking means attached to one of the plates and including a jacking screw registering with the guide bar therein, rotational movement of the jacking screw causing longitudinal movement of the guide bar along the slideway in which it is located and thereby effecting controlled translational movement of the other plate attached to the guide bar by the clamping screw.

7. A device according to claim 6, comprising:
a pair of jacking means attached to opposite ends of the slideway at the plate edges.

8. A prosthetic leg including a knee joint, and a shift device attached between the knee joint and a part of the leg, the shift device comprising:
first and second plates having adjoining flat faces in sliding contact;
an elongated slideway extending across an outer face of each plate to end at edges of the plate;
means guiding the slideways of the first and second plates for movement generally at right angles to one another, said guide means including first and second guide bars slideably received in the respective slideway;
means in each slideway defining at least one longitudinal slot whose length permits limited relative transitional movement of the plates; and
a clamping screw located freely in each slot of each of the first and second plates and engaging the guide bar in the slideway of the other plate, said clamping screw being releasable to allow relative movement of the plates and on re-tightening immobilising the plates.

9. A device according to claim 1, wherein:
one plate comprises at least one plain-sided hole having a larger diameter counterbore on the face of said one plate adjoining the other plate for the insertion of a screw for the attachment of the one plate to an adjacent limb part.

10. A device according to claim 9, wherein:
said other plate comprises a plain-sided hole having a diameter equal to the said larger diameter counterbore, the plain-sided hole in said other plate allowing access for a tool to turn said screw located in the hole in said one plate.

11. A device according to claim 9, wherein:
one plate comprises a plurality of plain-sided holes each having a large diameter counterbore.

12. A device according to claim 11, wherein:
said other plate comprises a plurality of plain-sided holes equal in number and spacing to said holes in the said one plate and each having a diameter equal to the said larger diameter counterbore, the plain-sided holes in said other plate allowing access for a tool to turn a screw located in each hole in said one plate.

13. A device according to claim 11, wherein:
four holes are provided in said one plate positioned to lie at the corners of a square.

14. A device according to claim 13, wherein:
an imaginary line of symmetry joining mid-points of two opposite sides of said square is offset relative to an imaginary central line of symmetry drawn across elongated closed slots in the plate in which said clamping screws are located to be received by the guide bars, whereby the plates are moveable between one extremity of their relative travel when the holes in one plate are aligned with holes in the other plate in one position and other extremities when the holes are aligned with other holes in said other plate, the total number of positions being four.

* * * * *